(12) United States Patent
Faris et al.

(10) Patent No.: US 6,734,436 B2
(45) Date of Patent: May 11, 2004

(54) OPTICAL MICROFLUIDIC DEVICES AND METHODS

(75) Inventors: Gregory W. Faris, Menlo Park, CA (US); John S. Bashkin, Fremont, CA (US); William H. Wright, Fremont, CA (US); Richard P. Heydt, Palo Alto, CA (US); David MacQueen, Half Moon Bay, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 10/215,355

(22) Filed: Aug. 7, 2002

(65) Prior Publication Data

US 2003/0047688 A1 Mar. 13, 2003

Related U.S. Application Data

(60) Provisional application No. 60/310,869, filed on Aug. 7, 2001.

(51) Int. Cl.[7] ............................................... G01N 27/26
(52) U.S. Cl. .................. 250/432 R; 250/428; 250/251; 250/453.11; 250/454.11; 250/455.11; 356/364; 204/450; 436/174; 436/518; 436/547; 436/527; 436/543; 359/566
(58) Field of Search ............................ 250/251, 453.11, 250/454.11, 455.11, 432 R, 428; 356/364; 204/450; 436/174, 518, 549, 527, 543; 359/566

(56) References Cited

U.S. PATENT DOCUMENTS

| 4,887,721 | A | * | 12/1989 | Martin et al. ................ 209/579 |
| 4,893,886 | A | | 1/1990 | Ashkin et al. |
| 5,100,627 | A | * | 3/1992 | Buican et al. ............... 422/108 |
| 5,512,745 | A | | 4/1996 | Finer et al. |
| 5,620,857 | A | | 4/1997 | Weetall et al. |
| 5,689,109 | A | | 11/1997 | Schütze |
| 6,055,106 | A | | 4/2000 | Grier et al. |
| 6,067,859 | A | | 5/2000 | Käs et al. |
| 6,139,831 | A | | 10/2000 | Shivashankar et al. |
| 6,159,749 | A | | 12/2000 | Liu |
| 6,180,940 | B1 | | 1/2001 | Galstian |
| 6,294,063 | B1 | * | 9/2001 | Becker et al. ............... 204/450 |
| 2001/0007775 | A1 | | 7/2001 | Seul et al. |
| 2001/0016361 | A1 | | 8/2001 | Seul et al. |

FOREIGN PATENT DOCUMENTS

WO    WO 01/01025    1/2001

* cited by examiner

Primary Examiner—John R. Lee
Assistant Examiner—David A. Vanore
(74) Attorney, Agent, or Firm—Louis L. Wu; Reed & Eberle LLP (57) ABSTRACT

The invention relates to microfluidic devices and methods that employ electromagnetic radiation to move a droplet of fluid on a fluid-transporting surface of a substrate. Typically, radiation of a particular wavelength is directed through a substantially transparent material, and the radiation imparts an optical trapping force to move the droplet. In addition, a means for reducing evaporative loss from the droplet may be provided.

86 Claims, 2 Drawing Sheets

OPTICAL MICROFLUIDIC DEVICES AND METHODS

CROSS-REFERENCE TO RELATED APPLICATION

This application claims priority to U.S. Provisional Patent Application Serial No. 60/310,869, filed Aug. 7, 2001.

ACKNOWLEDGMENT OF GOVERNMENT SUPPORT

This application was made in part with government support under contract number N66001-01-C-8057 awarded by Space and Naval Systems Center and Defense Advanced Research Projects Agency. The U.S. government has certain rights in the invention.

TECHNICAL FIELD

The present invention relates to the use of electromagnetic radiation to move droplets of fluid on a fluid-transporting surface. In particular, the invention relates to microfluidic devices and methods in which radiation is directed through a material that is substantially transparent to that radiation in order to optically move fluid droplets on a fluid-transporting surface. Typically, optical movement of fluid droplets is achieved while evaporative loss from the droplets is reduced.

BACKGROUND

A number of factors have contributed to the recent advances in the fields of biological sciences, biochemical assays, clinical diagnostics, and synthetic and analytical chemistry. These factors, for example, include the growing significance of genomics, the emergence of proteomics, and developments in combinatorial chemistry. In addition, the rise of drug-resistant forms of infectious diseases, increases in the incidence of food-chain contamination by pathogenic bacteria, the threat of biological warfare, and the continued prevalence of infectious diseases in underdeveloped countries also highlight the need for improved techniques for drug screening, drug target validation, toxicology studies, and combinatorial chemistry.

In these fields, progress has often been limited by the inability to process large numbers of samples at high speed. Extended time frames are necessitated by tedious sample preparation techniques and slow detection methods. These constraints in turn make automation of diagnostic assays difficult and create barriers to driving assay costs down. Thus, there is a current need in the art for rapid and inexpensive techniques to carry out diagnostics, parallel syntheses, and high throughput screening.

Expensive or rare fluids are employed in many emerging scientific applications, such as proteomics and genomics. Thus, considerable interest has been focused on microfluidic techniques, which typically involve small sample volumes and low reagent consumption. In addition, microfluidic techniques may be used to carry out numerous parallel processes, can be used across a range of fluid properties, and are compatible with movement of biological moieties that may vary by orders of magnitude in size and physical characteristics (e.g., from peptide hormones to intact cells). Processes in a microfluidic format are, therefore, particularly amenable to automation, enabling routine screening and surveillance programs to be established. In addition, new process paradigms, such as flow-through processing of biological samples, become feasible only in a microfluidic format.

A variety of microfluidic devices have been developed for chemical and bioanalytical applications. Typically, microfluidic devices involve the miniaturization and automation of a number of laboratory processes, which are then integrated on a chip. Thus, microfluidic technology may be employed to carry out a series of chemical or biochemical processes in a single device, including sample purification, separation, and detection of specific analytes. Applications include medical diagnostics, genetic analysis, or environmental sampling. See, e.g., Ramsey et al. (1995) "Microfabricated chemical measurement systems," *Nat. Med.* 1:1093–1096.

Microfluidic devices may be constructed using simple manufacturing techniques and are generally inexpensive to produce. For example, the microfabrication methods used to make microchips in the computer industry may also be used to create microfluidic devices, enabling the creation of intricate, minute patterns of interconnected channels. Once a pattern is created, microchip manufacturing methods are employed to recreate the channel design in a substrate. In some instances, chemical etching or stamping techniques are employed. As a result, highly precise channels with dimensions that can be varied in their width and depth may be produced on a substrate. Once the pattern is produced in the substrate, a cover plate is affixed over the substrate so as to form conduits in combination with the channels.

Typically, the substrates and/or cover plates are comprised of a rigid material such as glass (see, e.g., Woolley et al. (1994), "Ultra-high-speed DNA fragment separations using microfabricated capillary array electrophoresis chips," *Proc. Natl. Acad. Sci. USA* 91:11348–11352), plastic (see, e.g., McCormick et al. (1997), "Microchannel electrophoretic separations of DNA in injection-molded plastic substrates," *Anal. Chem.* 69:2626–2630), silicon, or quartz. Alternatively, microfabricated elastomeric valve and pump systems have been proposed in International Patent Publication No. WO01/01025. Similar valves and pumps are also described in Unger et al. (2000) "Monolithic microfabricated valves and pumps by multilayer soft lithography," *Science* 288:113–116. These publications describe soft lithography as an alternative to silicon-based micromachining as a means by which to form microfluidic devices. Through soft lithography, microfluidic structures created entirely from an elastomer may be constructed containing on/off valves, switching valves, and pumps.

The above-described microfluidic devices, however, pose certain technical challenges that must be overcome. For example, fluid flow characteristics within the small flow channels of a microfluidic device may differ from the flow characteristics of fluids in larger devices, since surface effects tend to predominate, and regions of bulk flow become proportionately smaller. Consequently, several techniques have been developed in order to achieve fluid flow control in microfluidic devices. One commonly used technique involves the generation of electric fields to manipulate buffered, conductive fluids around networks of channels through electrophoretic or electroosmotic forces. See, e.g., Culbertson et al. (2000), "Electroosmotically induced hydraulic pumping on microchips: differential ion transport," *Anal. Chem.* 72:2285–2291. Another technique, as described in Anderson et al. (2000), "A miniature integrated device for automated multistep genetic assays," *Nucleic Acids Res.* 28:E60, involves achieving fluidic control by coupling the device to an external system of solenoid valves and pressure sources.

The use of three-dimensional channels to define fluidic pathways, however, gives rise to several limitations. For example, leakage of fluids or analytes into undesired channels through diffusion or the influence of local electric field gradients requires the precise control of bias voltages along each channel in the microfluidic network. This need for precise control increases the design constraints for complex systems and requires that a high degree of engineering sophistication be incorporated into the microfabricated device. In particular, electric field gradients and path length differences around bends or corners in fluidic channels will also distort the distribution of analytes within the sample stream. This distortion can degrade the performance of an electrophoretic separation. In addition, the infrastructure and circuitry required to establish the electric fields are associated with certain spatial requirements that limit the complexity of the microfluidic devices. Furthermore, microvalves and other fluid control mechanisms greatly increase the complexity, cost, and manufacturability of such highly integrated designs.

In some instances, electric fields may be applied to move fluids without the use of three-dimensional channels. For example, U.S. Pat. No. 6,294,063 to Becker et al. describes microfluidic devices that programmably manipulate packets of fluids through the application of electric fields via electrodes located on the devices. A fluid is introduced onto a reaction surface and compartmentalized to form a packet. An adjustable programmable manipulation force is applied to the packet according to the position of the packet. As a result, the packet is programmably moved according to the manipulation force. In some cases, electromagnetic radiation may be used to maintain photochemical reaction or for sensing processes.

An alternative technique uses electric fields to effect fluid movement without channels and relies on the ability of electric fields to change the contact angle of a fluid on a surface (see, e.g., Lee et al. (2002), "Electrowetting and electrowetting-on-dielectric for microscale liquid handling," *Sensors and Actuators A* 95:259–268). Upon application of an electric field gradient to a droplet on a fluid-transporting surface, different contact angles are formed between leading and receding surfaces of the droplet with respect to the fluid-transporting surface. This imbalance in surface tension forces will produce a net force, and move the droplet. Other techniques have been explored for manipulating droplets of liquid on a substrate surface. For instance, Ichimura et al. (2000), "Light-driven motion of liquids on a photoresponsive surface," Science 288:1624–1626, describes placing a macroscopic droplet upon a particular surface polymer layer on a substrate, and using ultraviolet or blue light to change the isomeric form of the polymer layer. As a result, the contact angle between the droplet and the surface is changed, thereby moving the droplet. This approach is currently incapable of moving fluids at speeds exceeding about 35 µm/s, however, and it does not work with polar fluids.

Another technique involves the use of thermal gradients to move droplets of liquid. See, e.g., Kataoka et al. (1999), "Patterning liquid flow on the microscopic scale," Nature 402:794–797. The application of thermal gradients generates a thermocapillary shear stress at the air-liquid interface that is capable of driving a droplet across a surface. By the patterning of channels onto a surface, fluid movement can be precisely controlled. Another thermal gradient-driven approach, as described in Daniel et al. (2001), "Fast droplet movements resulting from the phase change on a gradient surface," *Science* 291:633–636, uses droplet coalescence to obtain droplet speeds of over 1 m/s. In either of these cases, however, the application of heat may not be suitable for some aspects of biological assays, and may exacerbate evaporation problems.

Optical trapping is a widely exploited phenomenon for manipulating items such as atoms, molecules, and small particles. The fundamental principle behind optical trapping is that light carries momentum, which can then be expressed as radiation pressure. When light is absorbed, reflected, or refracted by a material, momentum is transferred to the material. Optical tweezers have been developed that controllably deliver radiation pressure to manipulate small particles. Exemplary applications of optical tweezer technology include the manipulation of biological particles, such as cells, bacteria, and viruses (see, e.g., U.S. Pat. No. 4,893,886 to Ashkin et al. and U.S. Pat. No. 6,067,859 to Kas et al.), and the immobilization of biomolecules such as DNA, RNA, proteins, lipids, carbohydrates, or hormones (see U.S. Pat. No. 6,139,831 to Shivashankar et al.). While U.S. Pat. No. 6,294,063 to Becker et al. alludes to the use of optical tweezer technology for microfluidic manipulation, the microfluidic devices described require electrodes in order to apply electric fields that move the droplets and/or sense the position of the droplets. Since electrodes are generally opaque and do not allow the transmission of light therethrough, the microfluidic devices described in Becker et al. are generally incompatible with optical tweezer technology. As a result, optical trapping has not been successfully implemented in the field of microfluidics.

Thus, there exist opportunities in the field of microfluidics to employ optical techniques in order to controllably move fluids on a substrate surface.

SUMMARY OF THE INVENTION

In a first embodiment, an optical microfluidic device is provided, comprising a solid substrate, an electromagnetic radiation source, and a means for directing electromagnetic radiation. The solid substrate has a fluid-transporting surface and an opposing electromagnetic radiation-receiving surface, and is comprised of a material that is substantially transparent to electromagnetic radiation of a particular wavelength. The electromagnetic radiation source serves to generate electromagnetic radiation having the particular wavelength. The means for directing electromagnetic radiation is adapted to direct radiation generated by the source toward the radiation-receiving surface of the substrate. As a result, the directed electromagnetic radiation is transmitted through the substrate to the fluid-transporting surface in a manner effective to optically move one or more droplets of a selected fluid on the fluid-transporting surface from a first site to a second site.

In another embodiment, the invention provides an optical microfluidic device as above, except that the solid substrate is not necessarily comprised of a substantially transparent material. In such a case, an optically homogeneous cover plate is provided, comprising a material that is substantially transparent to electromagnetic radiation of the particular wavelength. In addition, the cover plate has an electromagnetic radiation-receiving surface and an opposing surface that faces the fluid-transporting surface. Accordingly, the means for directing electromagnetic radiation is adapted to direct radiation generated by the source toward the radiation-receiving surface of the cover plate. The directed electromagnetic radiation is transmitted through the cover plate to the fluid-transporting surface of the substrate in a manner effective to optically move one or more droplets of a selected fluid on the fluid-transporting surface from a first site to a second site.

In another embodiment, the invention provides an optical microfluidic device as generally described above except that neither a substantially transparent substrate or cover plate is required. Instead, the inventive device is comprised of a substrate (transparent or opaque) having a fluid-transporting surface, an electromagnetic radiation source, and a means for reducing evaporative loss of any droplet or droplets on the fluid-transporting surface.

In yet another embodiment, a method is provided for controllably moving a droplet of a selected fluid across a surface of a solid substrate. A droplet of a selected fluid is deposited on a first site of a fluid-transporting surface of a solid substrate. The substrate is comprised of a material that is substantially transparent to electromagnetic radiation of a particular wavelength. Then, electromagnetic radiation having the particular wavelength is directed toward a radiation-receiving surface that opposes the fluid-transporting surface of the substrate. As a result, the directed radiation is transmitted through the substrate to the fluid-transporting surface in a manner effective to optically move the droplet to a second site on the fluid-transporting surface.

In a further embodiment, a method is provided for controllably moving a droplet of a selected fluid across a surface of a solid substrate as described above, except that the substrate may not be substantially transparent. Instead, an optically homogeneous cover plate is provided comprising a substantially transparent material and having an electromagnetic radiation-receiving surface and an opposing surface. The cover plate is placed over the fluid-transporting surface, such that the opposing surface faces the fluid-transporting surface. Then, electromagnetic radiation is directed toward the radiation-receiving surface and through the cover plate to the fluid-transporting surface in a manner effective to optically move the droplet to a second site on the fluid-transporting surface.

In a still further embodiment, the invention provides methods for controllably moving a droplet of a selected fluid across a surface of a solid substrate as described above, except that the method additionally involves reducing evaporative loss from the droplet while the droplet is on the fluid-transporting surface. In this embodiment, the substrate may or may not be substantially transparent to light of the particular wavelength.

In yet another embodiment, the invention provides a method for controllably moving a fluid droplet across an interior surface of an enclosure, wherein the enclosure is formed at least in part by an optically homogeneous solid wall comprised of a material that is substantially transparent to electromagnetic radiation of a particular wavelength. A droplet of a selected fluid is deposited on the interior surface of the enclosure at a first site. Then, electromagnetic radiation of the particular wavelength is directed through the solid wall in a manner effective to optically move the droplet across the interior surface to the second site.

BRIEF DESCRIPTION OF THE DRAWINGS

FIGS. 1A–1C, collectively referred to as FIG. 1, schematically illustrate an embodiment of the inventive microfluidic device in which light is directed through a substantially transparent optically homogeneous cover plate to move a droplet of fluid on a fluid-transporting surface of a substrate.

DETAILED DESCRIPTION OF THE INVENTION

Before the invention is described in detail, it is to be understood that unless otherwise indicated, this invention is not limited to particular materials, components, or manufacturing processes, as such may vary. It is also to be understood that the terminology used herein is for purposes of describing particular embodiments only, and is not intended to be limiting.

It must be noted that, as used in the specification and the appended claims, the singular forms "a," "an," and "the" include plural referents unless the context clearly dictates otherwise. Thus, for example, reference to "a droplet" includes a single droplet as well as a plurality of droplets, reference to "a wavelength" includes a single wavelength as well as a plurality or range of wavelengths, reference to "a feature" includes one or more features, and the like.

In this specification and in the claims that follow, reference is made to a number of terms as defined to have the following meanings:

The term "array" as used herein refers to a two-dimensional arrangement of features on a substrate surface. Arrays are generally comprised of regular, ordered features, as in, for example, a rectilinear grid, parallel stripes, spirals, and the like, and they are distinguished from the more general term "pattern" in that patterns do not necessarily contain regular and ordered features.

The term "biomolecule" as used herein refers to any organic molecule—whether naturally occurring, recombinantly produced, or chemically synthesized in whole or in part—that is, was, or can be a part of a living organism.

The term "contact angle" as used herein describes the angle formed as a result of contact between a fluid and a solid surface, and reflects the interfacial affinity between the fluid and the solid surface, i.e., the wettability of the surface with respect to the fluid. When the fluid is in direct contact with the solid surface, the contact angle is at least 0° but less than 180°. A contact angle of 180° or greater indicates that the fluid is not in direct contact with the solid surface. In such a case, the fluid may indirectly contact the surface through an interposing fluid or may be levitated from the solid surface. The contact angle is inversely correlated with interfacial affinity. Thus, for example, a highly hydrophilic surface may form a low angle, e.g., 1°, with respect to water droplets. Similarly, a highly hydrophobic surface may form a high contact angle, e.g. 179°, with respect to water.

The terms "electromagnetic radiation" and "light" are used interchangeably herein, and are intended in their ordinary sense to refer to radiant energy of any wavelength associated with electric and magnetic fields resulting from the acceleration of an electric charge.

The term "fluid" as used herein refers to matter that is partially or fully liquid, although, when not fully liquid, may be partially solid and/or gaseous as well. A fluid may contain a solid that is minimally, partially, or fully solvated, dispersed, or suspended. Similarly, a fluid may contain one or more solvated gases. Examples of fluids include, without limitation, aqueous liquids (including water per se and buffer saline solutions) and nonaqueous liquids such as organic solvents and the like.

The term "fluid-constraining feature" as used herein refers to a chemical and/or physical formation that constrains fluid flow and optionally impedes flow of a selected fluid on a fluid-transporting surface. Fluid-constraining features include, but are not limited to, localized surface regions of relatively high affinity to the selected fluid, indentations, and channels.

The prefix "micro," as in "microfluidic device," refers to a device that can be used in any number of chemical processes involving very small amounts, i.e., "microscale" amounts, of fluid. Typically, fluids having a volume of about one microliter or less are transported in microfluidic devices. While certain microfluidic devices may be featureless, features contained in microfluidic devices typically have millimeter to submicrometer dimensions, and are adapted to the particular use of the microfluidic device.

The terms "optical" or "optically" are used herein in their ordinary sense and pertain to the branch of physical science that treats the nature and properties of electromagnetic radiation and the laws of its modification by opaque and transparent bodies. Accordingly, the term "optically move" as used herein refers to the application of optical trapping forces or radiation pressure to transfer momentum from electromagnetic radiation to an item, e.g., to a droplet of fluid, thereby moving the item. Similarly, the term "optically homogeneous" as used herein to describe an item such as a cover plate or a substrate refers to an item that is uniform with respect to electromagnetic radiation of at least one wavelength such that the entire item interacts with the radiation in the same manner. For example, an optically homogeneous substrate allows the same amount of light to be transmitted therethrough at any point.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "substantially" as in, for example, a material that is "substantially transparent to radiation of a particular wavelength" indicates that at least 90%, preferably at least 95%, more preferably at least 99%, and most preferably at least 99.9%, of the radiation of the particular wavelength received by the material is transmitted therethrough. Thus, a substantially transparent material may be completely transparent. Other uses of the term "substantially" involve an analogous definition.

The term "substrate" as used herein refers to any material having a fluid-transporting surface onto which one or more fluid droplets may be deposited and on which the droplets may be moved. The substrate may be constructed in any of a number of forms such as wafers, slides, or plates, for example. Optionally, the substrate further has an electromagnetic radiation-receiving surface that opposes the fluid-transporting surface.

The term "lubricating layer" refers to a layer that enhances fluid droplet mobility with respect to the fluid-transporting surface, and may include, for example, a solid layer with specific moiety or a liquid layer to increase the contact angle.

Thus, the present invention relates to devices and methods that employ electromagnetic radiation to move one or more fluid droplets on a fluid-transporting surface of a solid substrate, and is particularly suited for use in the field of microfluidics. Generally, microfluidic devices are formed from a solid substrate and an optional cover plate arranged over the substrate. The invention, when used in the microfluidic field, typically provides an electromagnetic radiation source to generate light of a particular wavelength, which is then directed through the substrate or the cover plate. The item through which the light is directed is substantially transparent to light of the particular wavelength. Preferably, the item is optically uniform with respect to light of the particular wavelength as well, because optical homogeneity advantageously provides improved control over optical droplet movement. While a certain amount of optical heterogeneity may be tolerated in microfluidic devices when light is used for detection or monitoring, optical trapping requires much more precise control over the light for optical movement. Optical heterogeneities may adversely affect optical trapping performance of a beam of light. In any case, through the application of appropriate optical control, light is transmitted to the fluid-transporting surface in a manner effective to optically move one or more droplets of a selected fluid on the fluid-transporting surface from a first site to a second site.

In general, all substrate and/or cover plate materials used should be chemically inert and physically stable with respect to any substance with which they come into contact during use. Suitable materials for forming the substrate include, but are not limited to ceramics, polymers, composites thereof, and laminates thereof. To take advantage of commercially available technologies, the substrate material may include materials normally associated with the semiconductor industry, in which such microfabrication techniques are regularly employed. For example, the substrate may be formed from silica-based materials such as glass or quartz. Similarly, commercially available ceramic materials such as aluminum oxide, zirconium oxide, titanium oxide, and the like may be employed as well. Further, suitable polymeric substrate materials will typically be organic polymers that are homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly (acrylonitrile-butadiene-styrene) (ABS), acrylate, acrylic acid polymers such as polymethyl methacrylate, other substituted and unsubstituted polyolefins, and copolymers thereof.

Although the fluid-transporting surface may have any contour suitable for microfluidic manipulation and movement, the fluid-transporting surface is preferably substantially planar. In addition, the interfacial affinity and surface tension between the fluid and the fluid-transporting surface is of particular importance. The interfacial affinity dictates the contact angle between the fluid and substrate and the droplet. To facilitate movement of fluid droplets on the fluid-transporting surface, the fluid-transporting surface typically repels the fluid droplets, i.e., forms a contact angle of greater than about 90°. Preferably, a contact angle of at least about 130° is formed between the fluid droplets and the fluid-transporting surface. More preferably the contact angle is at least about 150°. Optimally, the contact angle is at least about 170°. Such contact angles may be achieved, for example, by coating the fluid-transporting surface, at least in part, with a lubricating layer. Regardless of whether the lubricating layers are solid or fluid, they should not react with the selected fluid. Thus, lubricating layers, when provided as a fluid composition, should be both nonreactive and immiscible with the selected fluid.

In choosing a fluid lubricating layer, important considerations include viscosity, miscibility with the droplet fluid, and the resulting contact angle for the substrate/droplet interface at the lubricating layer interface. In certain circumstances, this contact angle can have theoretical contact angles in excess of 180°. For aqueous droplets, the lubricating layer will in general have some polar character to its surface tension to obtain the highest droplet/lubricating layer contact angle at the substrate. Both the dispersive and polar contributions to the surface tensions should be considered (see, e.g., Binks et al. (2002), "Solid wettability surface energy components: Relevance to Pickering Emulsions," *Langmuir* 18:1270–1273).

When a force is applied to a droplet on a fluid-transporting surface, different advancing and receding contact angles may be formed between the droplet and the fluid-transporting surfaces. The difference between advance and receding contact angles is referred to as contact angle hysteresis. In general, low contact angle hysteresis facilitates droplet movement. Thus, the contact angle hysteresis is preferably less than 2°. More preferably the contact angle hysteresis should be less than 1°. Optimally, the contact angle hysteresis should be less than 0.5°. Furmidge (1962), "Studies at phase interfaces 1. The sliding of liquid drops on solid surfaces and a theory for spray retention," *J. Colloid Sci.* 17:309–324, provides the following formula for the approximate force, F, needed to move a droplet $$F = \gamma_{LV}(\cos \theta_R - \cos \theta_A)d \quad (1)$$

where $\gamma_{LV}$ is the liquid-vapor surface tension, $\theta_R$ and $\theta_A$ are the advancing and receding contact angles, and d is the droplet contact perimeter.

Often, the selected fluid is aqueous. Thus, for aqueous droplets, a strongly hydrophobic surface may be used with the present invention. For example, with water droplets, a fluid lubricating layer may be provided on the fluid-transporting surface and comprised of a hydrophobic fluid composition. In addition, it should be noted that the fluid-transporting surface may be comprised of a plurality of regions, each exhibiting a different degree of affinity for the selected fluid, so as to form different contact angles with the selected fluid. Thus, at least a portion of the fluid-transporting surface may be comprised of a hydrophobic region.

Such regions may be formed by modifying a portion or the entirety of the fluid-transporting surface of the substrate. For example, the surface may be chemically and/or physically altered by an additive or subtractive process that changes one or more chemical and/or physical properties of a substrate surface or a selected site or region of a substrate surface. Surface modification may involve functionalizing or defunctionalizing a surface, i.e., by providing, modifying, substituting, or removing surface functional groups, or by otherwise altering the chemical composition of a surface.

In addition or in the alternative, surface modification may involve increasing or decreasing surface roughness, providing a coating on a surface (e.g., a coating that exhibits wetting properties that are different from the wetting properties of the surface) and/or depositing particulates on a surface. Thus, in order to render the fluid-transporting surface more hydrophobic, one may choose to bind a hydrophobic moiety that is bound to the fluid-transporting surface. Exemplary hydrophobic moieties may be selected from the group consisting of silanes, siloxanes, fluorosilanes, fluorosiloxanes, hydrocarbons, fluorocarbons, combinations thereof, and polymers and copolymers of any of the foregoing. In addition or in the alternative, the hydrophobic region may be provided as a textured surface, i.e., through additive or subtractive processes.

To enhance control over droplet movement, the device of the invention may further comprise a means for constraining the selected fluid. Generally, the means for constraining the selected fluid is adapted to constrain any droplet not being optically moved by the directed electromagnetic radiation. In some instances, the means for constraining the selected fluid may comprise a fluid-constraining feature on the fluid-transporting surface.

Different types of fluid-constraining features may be present on the fluid-transporting surface. For example, a fluid-constraining feature may be comprised of a first surface region circumscribing a second surface region, the second surface region exhibiting a higher degree of affinity for the selected fluid than the first surface region, such that the second surface region forms a smaller contact angle with the selected fluid than the first surface region. In addition or in the alternative, the fluid-constraining feature may comprise an indentation or protrusion on the fluid-transporting surface. In some instances, a plurality of fluid-constraining features may be provided on the fluid-transporting surface, and such fluid-constraining features may be arranged in an array on the fluid-transporting surface.

The preparation of substrates with well-defined regions of hydrophilic and hydrophobic domains has been well documented. Typical approaches involve the use photolithographic techniques to develop the spatial features, and silanization reagents to develop the desired surface properties. For example, a hydrophobic surface with isolated hydrophilic regions on a silica substrate is created by first applying a coating of a hydrophobic silanization agent, such as 1H, 1H, 2H, 2H-perfluorodecyltrichlorosilane, followed by illumination of the desired regions to remove the hydrophobic layer and expose the hydrophilic silica substrate. See, e.g., Kataoka et al. (1999), "Patterning liquid flow on the microscopic scale," *Nature* 402:794–797, and Daniel et al. (2000), "Fast droplet movements resulting from the phase change on a gradient surface," *Science* 291:633–636.

The surface properties of silane-modified substrates have been characterized in a number of papers. See, e.g., Brzoska et al. (1994), "Silanization of solid substrates: A step toward reproducibility," *Langmuir* 10:4367–4372, and Wasserman et al. (1989), "The structure of self-assembled monolayers of alkylsiloxanes on silicon: A comparison of results from ellipsometry and low-angle X-ray reflectivity," *J. Am. Chem. Soc.* 111:5852–5861. These papers describe conditions in which reproducible low surface energy, 6-mN/m (PTFE is 18 mN/m) monolayer coatings can be applied to silica substrates. In particular, it is described that preparation of such coatings may require proper cleaning of substrates and precise control of the water content, purity of the silane, and reaction temperature.

One way in which fluid-constraining features may be produced on a silica substrate surface is to first deposit a hydrophobic silane coating on the substrate surface. Then the hydrophobic silane coating may be selectively removed, e.g., using a mask and an excimer laser. Once the silane coating has been removed, the silica substrate will revert to its naturally hydrophilic state. The relative hydrophobicity of the resulting wells may be controlled by the quantity, depth and area of the coating removed.

Furthermore, the means for constraining the selected fluid may involve the application of optical, thermal, acoustic, electric field, magnetic, and/or physical forces sufficient to constrain the fluid. For example, multiple light beams may be used to create local traps that hold the droplets. These beams may be produced using a single light source and a partially opaque mask, a phase mask, or a holographic mask. When wave-like forces are used, interference between waves may be used to produce a regular pattern of constraining sites. In addition, the fluid droplets may be confined using electrostatic, electrophoretic, or dielectrophoretic means. These approaches use local application of electric fields to keep the droplets from moving. Another method for locating the wells is to use surface topography, i.e., to make the wells either depressed or elevated relative to the surrounding surface. It should be noted that a droplet's own inertia may contribute to its constraint.

Generally, any source of electromagnetic radiation may be employed with the invention as long as the source generates electromagnetic radiation capable of optically moving droplets of the selected fluid. In general, more intense light provides larger forces (and hence larger accelerations and faster motion), and a number of models have been developed to calculate the optical forces that may be exerted on small particles. Such models may be applied to fluid droplets as well. For example, forces on optically trapped droplets can be calculated to a first approximation by using models based either on ray-optics (valid for droplets much larger than the wavelength of light) or on electromagnetic dipoles (Rayleigh particles), which are much smaller than the wavelength of light. An exact ray-optics (RO) model, as described in Ashkin (1992), "Forces of a single-beam gradient laser trap on a dielectric sphere in the ray optics regime," *Biophys. J.* 61:569–582, is applicable when the droplet is much larger than the wavelength of the trapping beam. The relationship between trapping force and laser power is given by $$F=QnP/c \qquad (2)$$

where F is the force, Q is a nondimensional proportionality constant that describes the trapping efficiency of the beam as a result of the transfer of momentum from the laser beam to the microsphere, n is the refractive index of the surrounding medium (1.0 for air), P is the laser power, and c is the speed of light in free space. The efficiency parameter Q takes into account the influences that the convergence angle, spot size, wavelength, polarization, and beam profile have on the laser beam. It also takes into account the optical properties of the trapped object, including size, shape, and relative refractive index with respect to the surrounding medium. By convention, a negative value for Q indicates a trapping force.

Understanding how the laser beam and the droplet characteristics influence trapping is particularly useful because they can be used as design parameters to specify optimum droplets and beam geometries for trapping. From Equation (2), the trapping efficiency Q is simply the fraction of the momentum transferred to the sphere by the emergent rays. It is convenient to separate the resulting force on the droplet into scattering and gradient force components. The scattering force is due to the absorption and reradiation of light from an object, is proportional to the light intensity, and points in the direction of light propagation. In contrast, the gradient force represents the fluctuation of electric dipoles created as light passes through the trapped object. In this case, the force is proportional to the spatial gradient of light intensity and points in the direction of the gradient. Droplets that are much smaller than the wavelength of light are in the Rayleigh regime, and the equations that describe the scattering and gradient forces on the droplet are simplified. For example, the gradient force is proportional to the polarizability of the droplet multiplied by the spatial intensity gradient.

Neither ray optics nor the Rayleigh approximation is applicable, however, when the size of the trapped droplet is on the order of the wavelength of light (diameter<5 $\mu$m). Many examples of optical manipulation, including those that involve the smallest microdroplets, fall into this category.

The problem with optical manipulation of microdroplets has been solved by using models based on electromagnetic (EM) theory, which, in principle, should be exact regardless of the size of the trapped droplet. For weakly focused beams and large microspheres, EM and RO models are in agreement, according to Wright et al. (1993) "Radiation trapping forces on microspheres with optical tweezers," *Appl. Phys. Lett.* 63:715–717. To characterize the optical forces further, the peak transverse force has been measured by observing the speed at which the microsphere falls out of the optical trap in the presence of a drag force produced by the surrounding viscous medium. According to Wright et al. (1994) "Parametric study of the forces on microspheres held by optical tweezers," *Appl. Opt.* 33:1735–1748, experimentally measured values for Q agree with calculations to within 15% or better for both directions of motion relative to the laser beam polarization. This agreement gives confidence that the EM model is an accurate description of the optical trapping force.

One area of concern is that the surface of a fluid droplet might deform while exposed to the trapping beam. Ashkin et al. (1973), "Radiation pressure on a free liquid surface," *Phys. Rev. Lett.* 30:139–142, suggests that the radiation pressure on a liquid surface overcomes surface tension only when high peak powers (i.e., ~4 kW) from a pulsed laser are involved. At the low power levels applied continuously to the droplet, typically in the range of 1–100 mW, changes to the droplet shape are minimal. Deformation of the droplet as a function of the trapping power may be examined by monitoring the profile of the beam transmitted through the droplet and imaged onto a detector.

Typically, the particular wavelength corresponds to a wavelength that is minimally absorbed by the selected fluid. Light absorption tends to heat the droplets, enhances evaporative loss therefrom, and in some cases, may cause the droplets to degrade, particularly when the light is intense. According to Hale et al. (1973), "Optical constants of water in the 200-nm to 200-$\mu$m wavelength region," *Appl. Opt.* 12:555–563, water has a minimum absorption wavelength of about 480 nm. Accordingly, optical movement of aqueous fluids is generally preferred at or near this wavelength. Light at this wavelength can be produced directly using laser diodes, or through frequency doubling the wavelength of an infrared laser diode.

Thus, it should be noted that while polychromatic radiation may be employed, the light source, in some instances, may be selected for its ability to produce substantially monochromatic radiation of the particular wavelength. Diode lasers are preferred because of their low power consumption and compact size. However, other continuous wave sources may be used, such as an argon laser, a Ti:sapphire laser, or a dye laser. Alternatively, a light emitting diode (LED) or superluminescent LED may be used.

Preferably, a single source of electromagnetic radiation is employed along with a means for directing electromagnetic radiation. Such light directing means may be selected from the group consisting of mirror and galvo systems, acoustic-optic deflector systems, liquid crystal-based deflector systems, microelectromechanical (MEMS) mirror systems including micro-mirror arrays, and combinations of any of the foregoing. Improvements in MEMS-scannable mirrors will likely make these better than galvo mirrors and acousto-optic deflectors in the near future, due to their faster scanning rate and smaller size. Liquid crystal deflectors, as discussed in Johnson et al. (1993), "Smart spatial light modulators using liquid crystals on silicon," *IEEE J. Quantum Electron.* 29,699, are also suitable for directing electromagnetic radiation. Compact light directing means may be used to produce a hand-held microfluidic device.

As a general rule, a lens is employed to control the intensity profile of the directed light. In some instances, the directed radiation exhibits a Gaussian intensity profile. In other instances, the directed radiation exhibits a non-Gaussian intensity profile. In any case, optical movement may be achieved using radiation that exhibits a symmetric intensity profile, e.g., a rotationally or laterally symmetric intensity profile. Such symmetry is not required, however, as non-symmetric beams will still apply forces to droplets. It should be noted that the numerical aperture of the focusing lens influences the working distance for a given aperture diameter, the cost of the lens, and the flexibility in reaching the edges of the substrate. Because the substrate surface helps confine the droplet in the longitudinal direction, due to the combined effects of surface tension or surface adhesion, gravity, the physical mass of the substrate, and the radiation pressure provided by the light beam, it is not necessary to use very high numerical apertures to confine the droplets in the longitudinal direction, as is typical when optical tweezers are employed.

As discussed above, a plurality of droplets may be present on the fluid-transporting surface. Thus, the means for directing electromagnetic radiation may be adapted to optically move a plurality of droplets on the fluid-transporting surface. In some instances, the means for directing electromagnetic radiation may be adapted to optically move the droplets in succession. Alternatively, the means for directing electromagnetic radiation is adapted to optically move the droplets simultaneously. A variety of means may be used to move droplets simultaneously, for example as described in Visscher et al. (1996), "Construction of Multiple-Beam Optical Traps with Nanometer-Resolution Position Sensing," *IEEE Journal of Selected Topics in Quantum Electronics*, 2:1066–1076, Eriksen et al. (2002), "Fully dynamic multiple-beam optical tweezers," *Optics Express* 10:597–602, and references therein. These may be generally divided into spatially multiplexed and time multiplexed methods. In spatially multiplexed approaches, multiple beams are present at the same time. These beams may be produced using holograms, spatial light modulators, gratings, or other means. In temporally multiplexed techniques, a plurality of beams is produced by rapidly scanning a lesser number of beams such as by using mirror and galvo systems, acoustic-optic deflector systems, liquid crystal-based deflector systems, microelectromechanical (MEMS) mirror systems, or other means. This latter approach is sometimes refered to as a time share trap. All types of traps may be used to move droplets or to maintain droplet positions after moving, or even move the droplets gradually during an assay.

Droplet size is an important consideration for optical microfluidics. The droplet size influences the applied force, the relative sizes of the surface tension and volume forces, and the evaporation rate. The largest acceleration and deceleration possible for a given combination of droplet size, composition, and surface properties may be studied by using optical deflection to rapidly move the optical control beam at different rates and, thereby, determine the speed at which the beam and the droplet decouple. Thus, the invention is suitable for any droplet having a size that allows for its movement through optical trapping forces. That is, depending on the interaction between the directed light and the fluid droplet, varying degrees of momentum transfer may take place. Through ordinary electromagnetic radiation sources, one can usually optically move droplets having a volume of about 10 nanoliters or less with a fair degree of repeatability and precision. Repeatability and precision may be improved when the droplet has a volume of no greater than about 100 picoliters. Optimally, the droplet has a volume of no greater than about 1 picoliter, through in principle, there is no lower limit on the size of a droplet that may be moved using light.

In addition, the droplet may be of any composition that is optically movable. As discussed above, droplets may be formed from aqueous fluids such as water per se and buffered saline, as well as nonaqueous fluids such as dimethylsulfoxide and other organic solvents. Other compounds such as surfactants (e.g., anionic, cationic, nonionic, or amphoteric) and biomolecules (e.g., nucleotidic or peptidic) may be present in the droplet as well. It should be noted that the composition of the droplet and the presence of surfactants or other compounds in the droplet influence the surface wetting and, hence, the contact angle. The viscosity of the fluid will also influence the droplet motion in conjunction with the surface properties, (e.g., the degree to which droplets tend to slide or roll) and the mixing capabilities, as discussed below.

Furthermore, droplets employed in conjunction with the invention may take any of a number of different forms. While the invention may be used to optically move droplets comprised of vesicles, microspheres or liposomes, droplets for use with the invention are typically free from such items. In some instances, the droplet contains a plurality of solid particles. The particles may be located on a surface and/or the interior of the droplet. In some instances, solid particles may be advantageously used with a droplet to facilitate droplet movement on the fluid-transporting surface of the substrate. As an alternative or in addition to using surface coating to increase the contact angle formed between a droplet and the fluid-transporting surface, the droplet may be coated with solid particles. For example, aqueous droplets may be encapsulated with a hydrophobic powder. This technique has been described in Aussillous et al. (2001) "Liquid marbles," *Nature* 411:924–927. As result of encapsulation with a hydrophobic powder, the droplets form large contact angles (sometimes exceeding 180°), with the fluid-transporting surface, and adhesion between the droplets and the surface is greatly reduced.

Optionally, certain performance-enhancing features may be provided with the invention. For example, a means may be supplied for tracking and/or locating droplets on the fluid-transporting surface. Such means are particularly useful when a plurality of droplets are present on the fluid-transporting surface simultaneously. Such tracking and/or locating means are known in the art and may involve optical, electrical, magnetic, and/or radioactive monitors. U.S. Pat. No. 6,294,063 to Becker, for example, employs an impedance-sensing array to track and/or locate droplets on a substrate surface. Optical tracking of droplets may be performed using a charge-coupled device (CCD) or other imaging device viewing the fluid-transporting surface, optionally using the same lens as for the trapping radiation source.

Figure 1A:
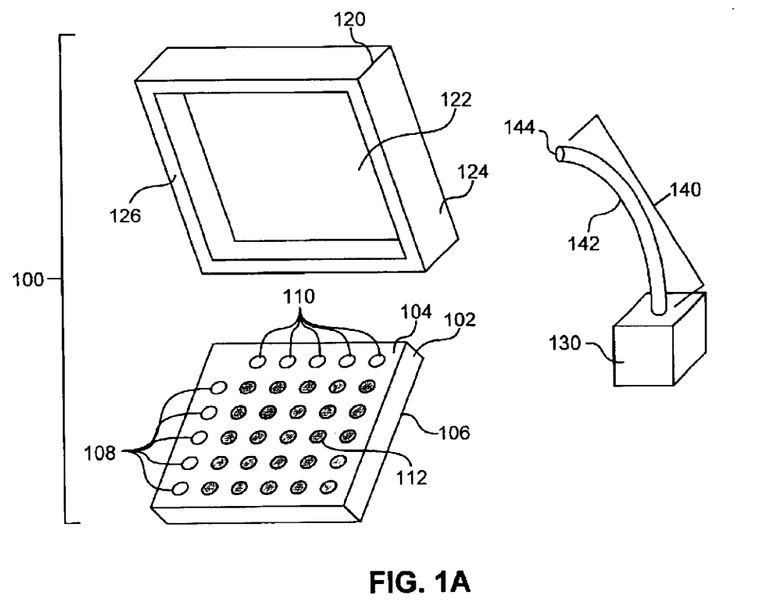
FIG. 1A schematically illustrates the device in exploded view.

FIG. 1 illustrates an example of the inventive device as described above for use with aqueous droplets. As with all figures referenced herein, in which like parts are referenced by like numerals, FIG. 1 is not necessarily to scale, and certain dimensions may be exaggerated for clarity of presentation. As illustrated in FIG. 1A, the device 100 includes a substrate 102 comprising upper and lower substantially planar opposing and parallel surfaces indicated at 104 and 106, respectively. The upper surface 104 serves as a fluid-transporting surface. The device 100 also includes a cover plate 120 that has lower and upper opposing and parallel surfaces indicated at 122 and 124. As shown, the substrate 102 and the cover plate 120 generally have similar construction, except that side wall 126 extends downward from lower surface 122 of the cover plate about its perimeter and is adapted to be placed in fluid-tight contact with upper surface 104 of the substrate 102. Also provided are a single electromagnetic source 130 and directing unit 140 comprised of an optical fiber 142 and a focusing lens 144 that serves as a means for directing electromagnetic radiation.

As depicted, the fluid-transporting surface has a plurality of surface regions. Generally, the entire surface 104 is hydrophobic. However, discrete fluid-constraining features are provided on the fluid-transporting surface 104 as sample reservoirs 108, reagent reservoirs 110, and reaction wells 112. Each feature is bounded by hydrophobic region 114. Although the sample reservoirs 108 and reagent reservoirs 110 are shown as two-dimensional features that are more hydrophilic than hydrophobic region 114 on the fluid-transporting surface 104, reservoirs may comprise any two-dimensional or three-dimensional container holding or containing a fluid. For example, a fluid-containing well of a well plate may serve as a three-dimensional reservoir. Similarly, a body of aqueous fluid constrained within a more hydrophilic surface region bounded by a hydrophobic surface region on a planar substrate surface may serve as a two-dimensional reservoir. Accordingly, each sample reservoir 108 contains a fluid sample droplet 116, while each reagent reservoir 110 contains a fluid reagent droplet 118. As depicted, sample reservoirs 108 and reagent reservoirs 110 are provided as linear arrays, and reaction wells 112 are provided as a two-dimensional rectilinear array.

Figure 1B:
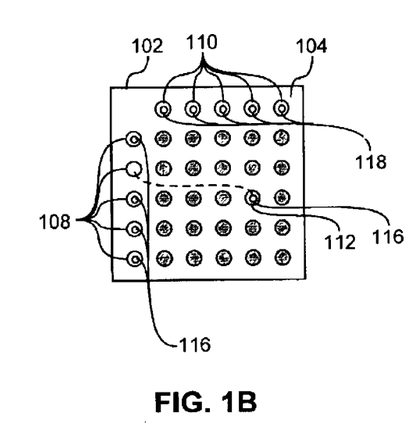
FIGS. 1B and 1C schematically illustrate in top view the movement of droplets from a sample fluid reservoir and a reagent reservoir, respectively, to a fluid-constraining feature.
Figure 1C:
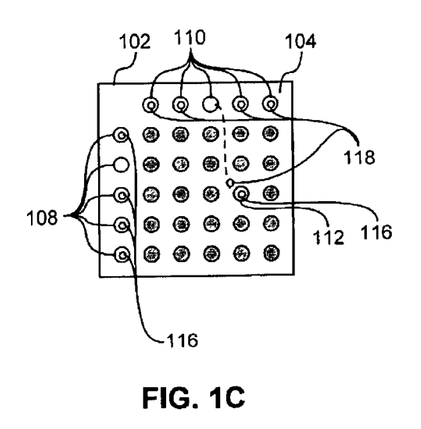

In operation, as depicted in FIGS. 1B and 1C, the cover plate is placed over the substrate 102, such that sidewall 129 is placed in fluid-tight contact with upper surface 104 of the substrate 102. The electromagnetic source 130 generates electromagnetic radiation of a particular wavelength that is directed by the optical unit 140 via the optical fiber 142 and lens 144 to the fluid-transporting surface 104 of the substrate 102. As this involves transmission of radiation through the substrate 102 and/or cover plate 120, one or both of the substrate 102 and the cover plate 120 are substantially transparent to the transmitted radiation. When the radiation is transmitted through the substrate 102, surface 106 serves as an electromagnetic radiation receiving surface. As shown in FIGS. 1B and 1C, however, the cover plate 120 is substantially transparent and optically homogeneous with respect to the transmitted radiation, and surface 124 serves as the radiation-receiving surface. Notably, the cover plate 120 may be placed over the substrate 102 at any time before light is used to optically move a droplet 116 or 118 on the fluid-transporting surface 104. That is, the cover plate 120 may be in place before, during or after a droplet 116 or 118 is placed on the fluid-transporting surface 104 of the substrate 102.

The directed radiation may be used to move any droplet to any well on the substrate. In FIG. 1B, radiation is directed to optically move a sample fluid droplet 116 from a sample reservoir 108 into the farthest well 112 along a defined path through region 114 on the fluid-transporting surface 104. As shown, the path in which the droplet is moved avoids any intervening wells. Once the droplet 116 is positioned within the well 112, light may be defocused or discontinued such that it ceases to optically trap the droplet 116. For example, the light source may be turned off or blocked with a shutter when the droplet is delivered to a desired site to prevent perturbing the droplet when the beam moves to the next droplet. Alternatively, droplet inertia may be used to minimize such perturbation, provided that the droplet is sufficiently large and the beam is moved away sufficiently rapidly. As a result, the droplet 116 is constrained solely by the relative hydrophilic surface of the well. Then, as depicted in FIG. 1C, radiation is directed to optically move a reagent fluid droplet 118 from a reagent reservoir 110 into the well 112 that contains the previously moved sample droplet 116. As a result, the sample fluid and the reagent contact each other and may react with each other.

As discussed above, the directed light may be incident from above the fluid transporting surface 104 of the substrate 102, as shown in FIG. 1, or from below. When the light illuminates from above, radiation pressure from the light beam is offset by the physical mass of the substrate, keeping droplets confined to the fluid transporting surface 104 of the substrate 102 regardless of the optical power or the numerical aperture of the focusing lens. When the directed light is incident from below, the droplets tend to be lifted from the fluid transporting surface 104. For sufficiently high light powers, droplets can even be levitated or otherwise moved away from the fluid transporting surface 104. See Ashkin (1997), "Optical trapping and manipulation of neutral particles using lasers," *Proc. Natl. Acad. Sci. U.S.A.* 94:4853–4860. Droplets will rise, moving away from the focus of the light beam until the radiation pressure drops to the level where it is equal to the weight of the droplet. Levitation of the droplets for motion has the advantage that cross-contamination is eliminated. The well sites may also be levitated. Levitation of well sites may also be performed using radiation pressure or other means including acoustic forces, electrostatic forces, or magnetic forces. Levitated traps may be produced using one light beam for each well or using time share traps.

Furthermore, the levitation height may be used to monitor droplet size. A feedback mechanism may be used to control the droplet height. In this case the droplet height is monitored, and circuitry is used to control the laser power to achieve a desired height above the substrate for all droplets. Monitoring the droplet height may be performed optically either by monitoring the amount of scattered light (which varies with beam intensity along the beam), perhaps in conjunction with a secondary means to monitor the droplet size (for example, by observing the transmitted beam size), or by viewing the droplet from the side.

Thus, in another embodiment, the invention provides a method for controllably moving a droplet of a selected fluid across a surface of a solid substrate. The method involves depositing a droplet of a selected fluid at a first site of a fluid-transporting surface of a solid substrate. Then, electromagnetic radiation having a particular wavelength is directed to the fluid-transporting surface in a manner effective to optically move the droplet to a second site on the fluid-transporting surface. When light is directed through the substrate, the substrate is comprised of a material that is substantially transparent to electromagnetic radiation of a particular wavelength. Similarly, an optically homogeneous cover plate may be provided comprising a substantially transparent material through which radiation can be directed.

Any of a number of means may be used to deposit the selected fluid on the fluid-transporting surface. For example, mechanical means for dispensing droplets include, without limitation, inkjet or bubble jet printer technology, printing pins (e.g. Telechem pins), pipettes, and syringes. Other technologies may be used to increase the rate of droplet production. For example, nebulizers may be used to produce a large number of droplets quickly. In addition, one may sonicate two immiscible liquids to produce layered droplets. In any case, a generally preferred means for generating small droplets involves the ejection of fluid through a small orifice, e.g., those associated with pipettes or micropipettes, with a pressure pulse. Droplet ejection may be enhanced by applying a coating to the orifice, e.g., by vapor deposition of a hydrophobic coating for aqueous droplets. Pressure pulses may be applied using a valve and a pressurized gas source, a piezoelectric crystal or other volume displacement means, or through volume expansion after rapid heating, e.g., by generating a gas bubble. Important issues for fluid deposition include standoff distance, orifice spacing, droplet size range, sample filling, and fluid compatibility.

An advantage of optical microfluidics is that the format of the dispensing means does not have to be identical to the format of the wells on the substrate. For example, multiple tip pipettes must have the same spacing as the wells in microtiter plates. This is not the case with optical microfluidics. Depending on the motion and shuttering capability of the electromagnetic radiation source and the means for directing radiation from the radiation source, the dispensing means and the substrate wells may have vastly different formats.

Other means may be used to effect fluid deposition. For example, various electrical or electromagnetic fluid deposition means are commercially available. In addition, photoisomerizable coatings may be advantageously used to induce fluid movement from a reservoir of fluid. For example, a terminus of a capillary may be coated with a material capable of undergoing photoisomerization that results in a change in the surface energy. The resultant change, for example, from hydrophilic to hydrophobic, will force the droplet out of the capillary for later manipulation. Changing the coating back to a hydrophilic state will reload the capillary. This approach also has the potential to deliver variable size droplets by simply repositioning the illuminated spot on the capillary. Light is directed by the means for directing electromagnetic radiation.

Beyond the basic transport of fluids, other functions may be performed with optical control. These include dispensing, droplet fusion (or merger) and splitting, mixing, heating, and sample purification. Functions such as dispensing, droplet fusion, and droplet splitting are influenced by the radiation and surface tension forces, as described below. One can use structured light fields or structured hydrophobic/hydrophilic surfaces to perform dispensing, fusion, and splitting. This, of course, means that the same or different contact angles may be formed between a droplet and the fluid-transporting surface at different locations and times.

One important microfluidic operation involves inducing droplets to collide with one another in order to merge the droplets. Typically, merged droplets will also mix. In general, it is not trivial to model the collision of droplets, even for two droplets colliding at a low Weber number (the ratio of inertial to surface tension forces). Tong (1996), "A numerical study on the collision behavior of droplets," *American Society of Mechanical Engineers, Fluids Engineering Division, FED* 238:397–402, reports the results of a computer simulation of droplet collisions that agree with experiments over a range of Weber numbers. The simulation is based on a two-dimensional, free-surface CFD solver developed at Los Alamos National Laboratory, as described in Kothe et al. (1991) "A computer program for incompressible flows with free surfaces," Report No. LA-12007-MS. Factors that affect droplet-droplet impact include surface tension and droplet/surface contact angle, droplet size, evaporation effects, droplet fluid viscosity, the effects of different fluid types, and the use of surfactants in the sample or reagent. As for cell-cell fusion, various means may be used to enhance droplet-droplet fusion, including laser pulses, electrical pulses, chemical mechanisms, or biological mechanisms (see, e.g., Steubing et al. (1991), "Laser induced cell fusion in combination with optical tweezers: the laser cell fusion trap," *Journal of Membrane Biology*, 12:505–510, and Baumann (2002), "Cell Fusion Generates an Inhomogeneous Distribution of Elasticity and Rigidity in Plasma Membranes," *Journal of Membrane Biology* 1:148, and references therein).

Mixing may also be enhanced by rotation of droplets using light. Optically trapped droplets can be rotated if the droplet is absorbing, if the trapping beam is circularly polarized, or by using phase-patterned light. If the incident light is circularly polarized, a torque is induced on the droplet in the absence of absorption, regardless of its location in the trap. The theoretical radiation torques for spherical particles have been calculated in Marston (1984), "Radiation torque on a sphere illuminated with circularly polarized light," *J. Opt. Soc. Am. B* 1:528–529, Marston et al. (1984), "Radiation torque on a sphere caused by a circularly-polarized electromagnetic wave," *Physical Review A: Atomic, Molecular, and Optical Physics* 30:2508–2516, and Chang et al. (1985), "Optical torque exerted on a homogeneous sphere levitated in the circularly polarized fundamental-mode laser beam," *J. Opt. Soc. Am. B* 2:1853–1860. According to Chang et al. (1985), "Optical torque exerted on a homogeneous sphere levitated in the circularly polarized fundamental-mode laser beam," *J. Opt. Soc. Am. B* 2:1853–1860, these calculations have generally been experimentally verified using circularly polarized light applied to small homogeneous spheres.

Other papers also discuss the use of light to rotate spherical particles. For example, it is reported in Chang et al. (1988), "Radiation force and torque exerted on a stratified sphere in the circularly polarized $TEM_{01}$-mode laser beam," *J. Opt. Soc. Am. B* 5:61–66, that theoretical expressions have also been developed for the torque on a stratified sphere illuminated by a circularly polarized $TEM_{01}$ mode laser beam. In addition, Paterson et al. (2001), "Controlled rotation of optically trapped microscopic particles," *Science* 292:912–914, describes an alternative technique for spinning non-absorbing droplets by using the interference pattern formed as a result of the interaction between an annular shaped laser beam and a reference beam. For absorbing spherical droplets, torques also can be induced by linearly polarized light. In the absence of absorption, all forces are normal to the particle surface and act through the center of the particle. However, for an absorbing droplet that is displaced along a first axis (x-axis) by a laser beam propagating along a second axis (z-axis), optical trapping creates a torque about a third axis (y-axis) that is orthogonal to the first and/or the second axes. Factors important to droplet rotation include refractive index, droplet size and viscosity, beam intensity profile, and numerical aperture.

A number of techniques may be employed to determine the rate and/or extent of mixing. For example, a two-component system may be used. In some instances, such a two-component system may employ a metal chelate complex. In order to monitor the mixing behavior of two droplets, one droplet may contain a chelating ligand, while the other may contain a metal ion. By monitoring the formation of the metal chelate complex, mixing behavior of the two droplets can be determined. Another similar approach involves the use of fluorescence quenching to monitor the extent of mixing. In such a case, a fluorescent probe is inserted into one droplet and the quencher is placed into the other droplet. By determining the emission intensity profile as a function of time, one can determine the mixing rates and efficiency of mixing. In this manner, one can monitor various parametric effects such as droplet size and viscosity.

Optical forces may be used for droplet splitting. Splitting may be necessary to dispense a droplet from a reservoir of a large body of fluid. Generally, droplet splitting is a complex matter involving precise control and balance over various factors. Factors that affect droplet splitting include, for example, surface tension and droplet/surface contact angle, droplet size, evaporation effects, droplet fluid viscosity, the effects of different fluid types and use of a surfactant in the sample or reagent, and the source of the light beam (power, wavelength, and numerical aperture). In particular, one important challenge associated with droplet splitting is to overcome the potential barrier that occurs when a secondary droplet necks down before actually splitting from the primary droplet. This barrier can be reduced through the use of physical enhancements. For example, in the process of drawing droplets from a capillary with light, the necking-down has already been achieved; thus, the barrier is reduced.

An alternative to lowering the barrier is to enhance the optical force supplied by the light beam through storage of kinetic energy. By accelerating a droplet using the light beam and then impinging the accelerated droplet onto a surface, a force much larger than the optical force can be applied to the droplet. For example, a droplet may be accelerated toward a sharp solid edge and split upon impact therewith. In essence, the edge serves as a knife that separates the droplet in two. In order to produce such an edge for small droplets, ordinary microfabrication techniques such as photolithography may be employed. Once a droplet is split into two, constraining means may be used to capture the droplets and to dissipate the momentum imparted during acceleration. In some instances, the constraining means can be provided in the form of additional barriers and/or surfaces features. For example, surface features may be comprised of a surface region that exhibits increasing attraction to the droplet as the droplet moves away from the edge. That is, the contact angle between the droplet and the surface decreases as the droplet moves away from the edge. As a result, the shape of the droplet will become less spherical and more puddle-like, and the increasing surface/droplet affinity will serve to slow the droplet. Similarly, an inclined surface may also serve to slow the droplet.

Heating or thermal cycling of droplets is important for certain applications, such as the polymerase chain reaction (PCR) for DNA amplification. Droplets may be heated by using a second laser wavelength that is absorbed by the droplet or solute in the droplet, or by tuning the laser wavelength. The output of the 1.55-$\mu$m diode lasers used for optical communications are strongly absorbed by water and would be very effective for droplet heating. The heating is influenced by the optical absorption coefficient, droplet volume, and environmental conditions. In order to promote thermal uniformity throughout a droplet, one may actively spin or mix the droplet during the heating and cooling cycles, as discussed above. This would increase the speed of temperature transitions and thereby improve the speed and quality of the PCR steps.

A variety of means for monitoring temperatures in laser traps are known in the art and have been described, for example, in Celliers et al. (2000), "Measurement of localized heating in the focus of an optical trap," *Appl. Opt.* 39:3396–3407. In some instances, temperature-sensitive dyes may be employed; a droplet will be produced at the appropriate dye concentration. The greatest accuracy will be obtained when using at least two beams of electromagnetic radiation for these measurements: one to heat the droplet and one to interrogate the dye. For example, a 1.55-$\mu$m diode laser may be used to heat the droplet, and an argon ion laser to excite the dye. By using the inherent absorption of the droplet at 1.55 $\mu$m, there is no need for an additional chromophore to heat the dye, which might lead to quenching of the temperature-reporting function. One can also monitor the reduction in droplet size with and without heating. With appropriate consideration of the Kelvin and solute effects, this provides another way to monitor droplet heating.

The invention may also be adapted to engage in purification and/or separation processes. For example, samples moieties within a fluid droplet may be purified through selective application of optical forces. When sample moieties are present as a solute in a droplet, one may choose to employ light of a wavelength near an absorption resonance of the moiety. As a result, the optical force on the solute is enhanced relative to the solvent. Then, by applying a light gradient, one can preferentially collect the solute in the high intensity region of the light beam. By following this process with splitting of the droplet, one can achieve sample purification.

In addition, sample moieties within a fluid droplet may be purified through interaction with the fluid-transporting surface. In general, different surfaces may interact differently toward a sample moiety, and sample fluids may be purified by exploiting the differential diffusion of sample moieties on different surfaces. This separation is based on the mass action law, which correlates the mass of a moiety that binds to a surface and time to the diffusion rates, concentration, and binding constants of analyte and capture ligand. Optical microfluidics may be used to incorporate several post mixing processes, such as sample concentration, purification, and assay performance. Potentially, all these processes can be readily achieved by moving a droplet in a controlled manner across a surface having a capture zone that is functionalized to facilitate the desired process. Thus, while a droplet is moved across a fluid-transporting surface in an appropriate path, a moiety within the droplet may selectively bind to the capture zone. For example, when a droplet containing DNA is moved across a hydrophobic surface designed to nonspecifically capture DNA, the DNA may be removed from the droplet as the droplet is displaced, thereby producing a purified DNA sample on the surface. Then, another droplet containing a release agent (e.g., a highly saline solution) may be moved over the captured DNA, and the purified DNA thus removed for further processing.

Alternatively, the fluid-transporting surface may be modified with a ligand, natural or synthetic, to selectively capture specific DNA. The same process should be applicable to any component in the sample that can be selectively bound. An analogous procedure could be used to concentrate a desired component of the analyte solution by passing several droplets over the capture zone. Heat may also be applied for selective adsorption or desorption.

Accordingly, the invention may be used to carry out certain assays that involve the interaction of the fluid-transporting surface with droplets. For example, in the case of nonspecifically bound DNA, once the DNA has been immobilized on the surface, another droplet is introduced containing a fluorescently labeled DNA probe, such as one that is implicated in an infectious disease or a genetic disorder. After incubation and washing, the capture zone is illuminated, and the fluorescence response indicates the presence (or absence) of the target. Other applications may be found in the fields of proteomics and genomics, for example, in which protein-protein interactions are determined for a droplet that is moved across several different capture zones. Droplets containing fluorescently labeled ligands that have known affinities for a specific protein would then be moved across all the capture zones, thus indicating where the target protein had bound.

An important issue to consider when conducting assays is the nonspecific binding potential of the target or reagent to the substrate. For example, aqueous droplets are typically moved over hydrophobic fluid-transporting surfaces. Although the hydrophobic surface minimizes the droplet-substrate interface and allows for easier movement of the droplet, certain moieties, including hydrophobic proteins, may be nonspecifically bound to such surfaces. One method by which to minimize the effects of nonspecific binding and cross-contamination is to use fluid transport paths that have minimal crossing points. For example, droplets following parallel paths can have slight offsets such that they don't travel over the identical paths.

Many assays use light for detection through measurement of fluorescence, color change, polarization change, and/or refractive index change. The same light beam, lens, or means of directing radiation used to move and/or heat droplets may also be used to detect changes in the droplet and/or on the fluid-transport surface. Such changes may, for example, be associated with the presence of specific analytes, a chemical or biological binding event, a chemical or biological reactions, or other changes. Optionally, the wavelength of the beam used for droplet motion may be chosen to minimize potential photobleaching of any fluorescent labels used for detection.

Due to the small droplet sizes involved in optical microfluidics, evaporation is also an important factor to consider. Thus, in another embodiment, the invention provides an optical microfluidic device that includes a means for reducing evaporative loss from a fluid droplet of a selected fluid on a fluid-transporting surface of a solid substrate. As is the case with the embodiments of the inventive device described above, this microfluidic device includes an electromagnetic radiation source for generating electromagnetic radiation and a means for directing the electromagnetic radiation generated by the source toward the fluid-transporting surface in a manner effective to optically move at least one droplet of a selected fluid on the fluid-transporting surface from a first site to a second site. It is not critical whether the light is directed to the fluid-transporting surface from above or below.

In some instances, the means for reducing evaporative loss is comprised of a vapor-blocking layer that is substantially impermeable to the selected fluid in vapor form, wherein the vapor-blocking layer is positioned in facing and, optionally, contacting relationship with respect to the fluid-transporting surface. In some instances, the vapor-blocking layer may be comprised of a fluid composition that is nonreactive and immiscible with the selected fluid. For example, when an aqueous droplet of fluid is present on the fluid-transporting surface, an overlying oil layer serves as the vapor-blocking layer. In many cases the fluid composition intended for use as a blocking layer will have a higher refractive index than that of the droplet. In this case a conventional $TEM_{00}$ beam will repulse the droplet away rather than attract or trap the droplet. The optical trapping beam may have a $TEM_{01}$ or doughnut mode to properly trap the droplets when a higher refractive index fluid vapor-blocking layer is employed. Alternatively, a beam with a crescent, v-shape, or, any other shape may be used to move the droplet in a "push-broom" fashion. In any case, when a fluid vapor-blocking layer is used, a cover plate facing the fluid-transporting layer of the substrate may be provided, and the vapor-blocking layer is then interposed between the cover plate and the substrate. Such a cover plate may serve to control the surface contour of the vapor-blocking fluid. Alternatively the vapor-blocking layer may be comprised of a solid material. If it is desired that the optical trapping beam be transmitted through the vapor-blocking layer, the vapor-blocking layer should be comprised of a substantially transparent material that is optically homogeneous with respect to electromagnetic radiation of the particular wavelength.

Liquids that are immiscible with the droplet liquid may still have the capability to dissolve a small quantity of the droplet liquid. In this case, it is preferable to saturate such vapor-blocking liquids with the droplet liquid to prevent or mitigate losses in the droplet volume.

Important physical principles that affect the evaporation are the curvature (or Kelvin) effect, which leads to a higher vapor pressure for smaller droplets; and the solute effect, which leads to a lower vapor pressure for smaller droplets. Other factors influencing the evaporation from a droplet of a selected fluid comprising a solute in a solvent include, for example, the droplet solvent type, solute content, and the presence of the solvent in vapor form. Thus, the means for reducing evaporative loss is comprised of a means for introducing the selected fluid in vapor form at or near the fluid-transporting surface.

Figure 2:
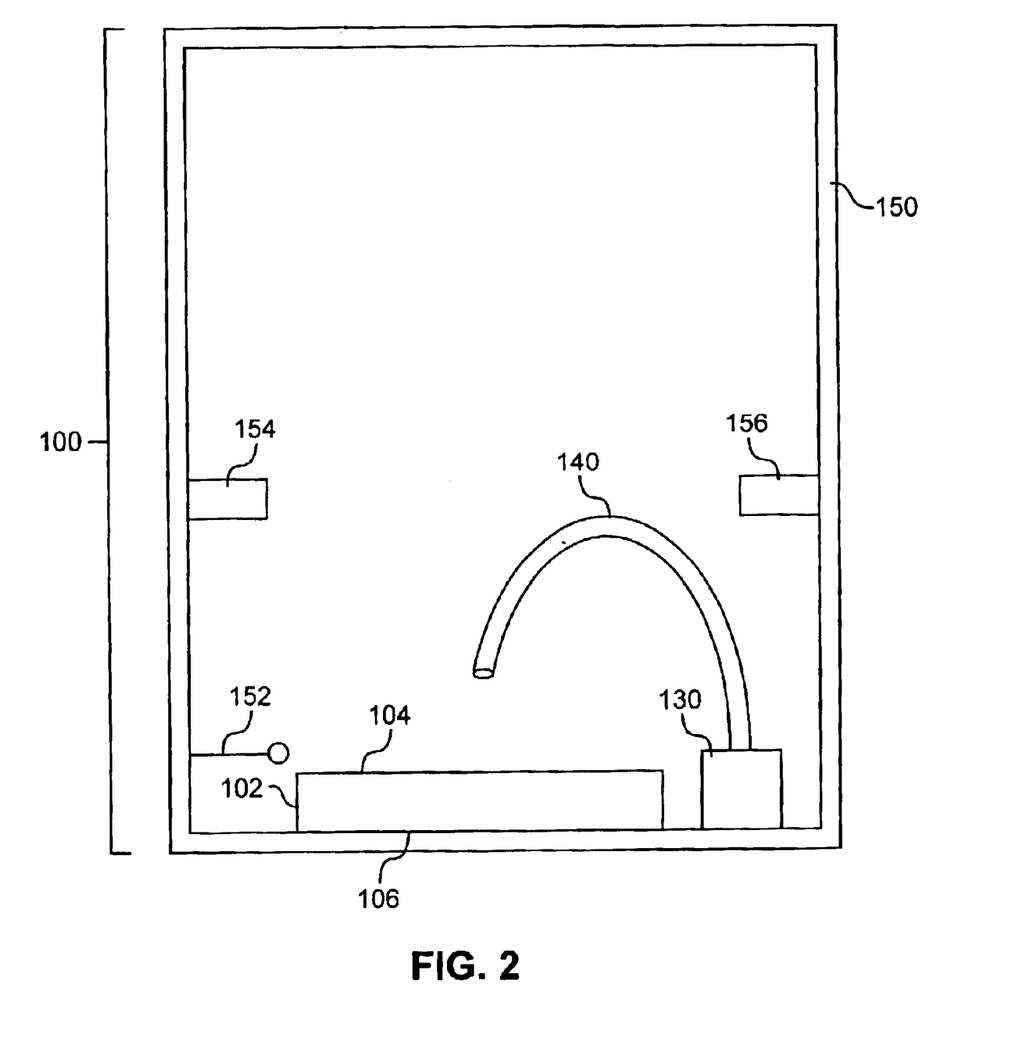
FIG. 2 schematically illustrates in cross-sectional view another embodiment of the inventive device having a means for reducing evaporative loss.

FIG. 2 illustrates an example of the inventive device for optically moving aqueous droplets in the presence of a humidity controller. As before, the device 100 includes a substrate 102 comprising upper and lower substantially planar opposing and parallel surfaces, indicated at 104 and 106, respectively. The upper surface 104 serves as a fluid-transporting surface. In addition, an electromagnetic source 130 and a directing unit 140 are provided. The substrate 102, electromagnetic source 130, and the directing unit 140 are enclosed in a humidity-controlled environmental chamber 150. The humidity within the chamber 150 may be controlled actively using a humidity sensor 152 and a means to increase humidity 154, such as a nebulizer, atomizer, or heated water source. Optionally, a dehumidifier 156 is employed as well to maintain strict and precise control over the humidity. It is preferred that the humidity sensor be placed near the fluid-transporting surface to accurately monitor the humidity of the local environment of the droplets. Humidity control chambers are available from a number of commercial sources such as Tenney Environmental (Parsippany, N.J.) and Thermotron Industries (Holland, Mich.).

Alternatively, humidity may be controlled passively by coupling the headspace over the droplets to a larger water reservoir maintained at a fixed temperature. Another way in which the influence of evaporation may be reduced is to periodically add new aliquots of liquid to each droplet in the array of wells. This process is similar in concept to the "refresh" for semiconductor memories. Finally, because of the higher mixing and reaction rates of the small droplets, the significance of evaporation can be greatly reduced. That is, assays or procedures can be performed rapidly, as compared with the evaporation rate. Droplet evaporation may be studied by monitoring the droplet diameter as a function of time, both with and without laser illumination.

The present invention thus provides devices and methods that employ electromagnetic radiation to move fluid droplets on a solid substrate surface. A number of important—and heretofore unrealized (or not fully realized)—advantages have now been achieved in the field of microfluidics. Such advantages include:

Low complexity on substrate. The substrate can be manufactured easily at low cost, thereby rendering disposability economically feasible.

Random access. Because any reservoir can be coupled to any well, greater flexibility is possible for performing an assay.

Flexible delivery. The assay may be readily configured through software control of the light beams to adapt to new measurement requirements or to incorporate new assay protocols.

Scalability. Because there are no valves or cross-T injectors, optical microfluidics can be readily scaled to larger numbers of assays per chip.

Efficiency. The light beam can operate on the precise amount of liquid to be delivered to the well; no excess liquid is left in a delivery channel.

Compactness. No "real estate" on the chip is devoted to channels or supporting circuitry.

High speed. The controlling light beams can be moved rapidly without macroscopic moving parts.

Flexible formats. The format or spacing of droplet dispensing does not need to match the format or spacing of the wells, because the light beams can change the format during delivery to the wells. This facilitates the interface between the macroenvironment of the initial sample and microenvironment of the assay.

High functionality. Light may be used for many other functions beyond simple fluidic transport, such as dispensing, droplet splitting, droplet fusion, heating or thermal cycling, active mixing, sample purification and detection. This rich palette of functionality enables creation of very powerful yet simple and compact microanalysis systems.

Thus, variations of the present invention will be apparent to those of ordinary skill in the art. It is to be understood that, while the invention has been described in conjunction with the preferred specific embodiments thereof, that the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

What is claimed is:

1. An optical microfluidic device, comprising:
a solid substrate comprised of a material that is substantially transparent to electromagnetic radiation of a particular wavelength, the substrate having a fluid-transporting surface and an opposing electromagnetic radiation-receiving surface;
an electromagnetic radiation source for generating electromagnetic radiation having the particular wavelength; and
a means for directing electromagnetic radiation generated by the source toward the radiation-receiving surface and through the substrate to the fluid-transporting surface in a manner effective to optically move at least one droplet of a selected fluid on the fluid-transporting surface from a first site to a second site.

2. The device of claim 1, wherein the means for directing electromagnetic radiation is adapted to optically move a plurality of droplets on the fluid-transporting surface.

3. The device of claim 2, wherein the means for directing electromagnetic radiation is adapted to optically move the droplets in succession.

4. The device of claim 2, wherein the means for directing electromagnetic radiation is adapted to optically move the droplets simultaneously.

5. The device of claim 1, further comprising a means for tracking and/or locating the at least one droplet.

6. The device of claim 1, wherein the fluid-transporting surface is substantially planar.

7. The device of claim 6, wherein the fluid-transporting surface and the radiation-receiving surface are parallel to each other.

8. The device of claim 1, wherein the substrate is optically homogeneous with respect to electromagnetic radiation of the particular wavelength.

9. The device of claim 1, wherein the fluid-transporting surface is comprised of a plurality of regions, each exhibiting a different degree of affinity for the selected fluid so as to form different contact angles with the selected fluid.

10. The device of claim 1, further comprising a means for constraining the selected fluid.

11. The device of claim 10, wherein the means for constraining the selected fluid is adapted to constrain any droplet not being optically moved by the directed electromagnetic radiation.

12. The device of claim 10, wherein the means for constraining the selected fluid comprises a fluid-constraining feature on the fluid-transporting surface.

13. The device of claim 12, wherein the fluid-constraining feature is comprised of a first surface region circumscribing a second surface region, the second surface region exhibiting a higher degree of affinity for the selected fluid than the first surface region such that the second surface region forms a smaller contact angle with the selected fluid than the first surface region.

14. The device of claim 12, wherein the fluid-constraining feature comprises an indentation or protrusion on the fluid-transporting surface.

15. The device of claim 12, comprising a plurality of fluid-constraining features on the fluid-transporting surface.

16. The device of claim 15, wherein the fluid-constraining features are arranged in an array on the fluid-transporting surface.

17. The device of claim 1, wherein the fluid-transporting surface is coated at least in part with a lubricating layer.

18. The device of claim 17, wherein the lubricating layer is comprised of a fluid composition that is nonreactive and immiscible with the selected fluid.

19. The device of claim 18, wherein the fluid composition is hydrophobic.

20. The device of claim 1, wherein at least a portion of the fluid-transporting surface is comprised of a hydrophobic region.

21. The device of claim 20, wherein the hydrophobic region comprises a hydrophobic moiety bound to the fluid-transporting surface.

22. The device of claim 21, wherein the hydrophobic moiety is selected from the group consisting of silanes, siloxanes, fluorosilanes, fluorosiloxanes, hydrocarbons, fluorocarbons, combinations thereof, and polymers and copolymers of any of the foregoing.

23. The device of claim 20, wherein the hydrophobic region is a textured surface.

24. The device of claim 1, wherein a contact angle of at least about 130° is formed between the at least one droplet and the fluid-transporting surface.

25. The device of claim 24, wherein the contact angle is at least about 150°.

26. The device of claim 25, wherein the contact angle is at least about 170°.

27. The device of claim 1, wherein the source of electromagnetic radiation produces substantially monochromatic radiation.

28. The device of claim 27, wherein the source of electromagnetic radiation is a laser.

29. The device of claim 1, wherein the source of electromagnetic radiation is a light emitting diode.

30. The device of claim 1, comprising a single source of electromagnetic radiation.

31. The device of claim 1, wherein the particular wavelength corresponds to a wavelength that is minimally absorbed by the selected fluid.

32. The device of claim 1, wherein the means for directing electromagnetic radiation is selected from the group consisting of mirror and galvo systems, acoustic-optic deflector systems, liquid crystal-based deflector systems, microelectromechanical mirror systems, and combinations of any of the foregoing.

33. The device of claim 1, further comprising a means for reducing evaporative loss from the at least one droplet of the selected fluid.

34. The device of claim 33, wherein the means for reducing evaporative loss is comprised of a vapor-blocking layer that is substantially impermeable to the selected fluid in vapor form, wherein the vapor-blocking layer is positioned in facing and, optionally, contacting relationship with respect to the fluid-transporting surface.

35. The device of claim 34, wherein the vapor-blocking layer is comprised of a fluid composition that is immiscible and nonreactive with the selected fluid.

36. The device of claim 34, wherein the vapor-blocking layer is comprised of a solid material.

37. The device of claim 1, further comprising a means for introducing the selected fluid in vapor form at or near the fluid-transporting surface.

38. The device of claim 1, wherein the selected fluid is aqueous.

39. An optical microfluidic device, comprising:
a solid substrate having a fluid-transporting surface;
an optically homogeneous cover plate comprised of a material that is substantially transparent to electromagnetic radiation of a particular wavelength, the cover plate having an electromagnetic radiation-receiving surface and an opposing surface that faces the fluid-transporting surface;
an electromagnetic radiation source for generating electromagnetic radiation having the particular wavelength; and
a means for directing electromagnetic radiation generated by the source toward the radiation-receiving surface and through the cover plate to the fluid-transporting surface in a manner effective to optically move at least one droplet of a selected fluid on the fluid-transporting surface from a first site to a second site.

40. An optical microfluidic device, comprising:
a solid substrate having a fluid-transporting surface;
an electromagnetic radiation source for generating electromagnetic radiation; and
a means for directing electromagnetic radiation generated by the source toward the fluid-transporting surface in a manner effective to optically move at least one droplet of a selected fluid on the fluid-transporting surface from a first site to a second site; and
a means for reducing evaporative loss from the at least one fluid droplet.

41. The device of claim 40, wherein the fluid-transporting surface is substantially planar.

42. The device of claim 40, wherein the selected fluid is aqueous.

43. The device of claim 40, wherein the means for reducing evaporative loss is comprised of a vapor-blocking layer that is substantially impermeable to the selected fluid in vapor form, wherein the vapor-blocking layer is positioned in facing and, optionally, contacting relationship with respect to the fluid-transporting surface.

44. The device of claim 43, wherein the vapor-blocking layer is comprised of a fluid composition that is nonreactive and immiscible with the selected fluid.

45. The device of claim 44, further comprising a cover plate facing the fluid-transporting layer of the substrate, wherein the vapor-blocking layer is interposed between the cover plate and the substrate.

46. The device of claim 43, wherein the vapor-blocking layer is comprised of a solid material.

47. The device of claim 43, wherein the vapor-blocking layer is comprised of a substantially transparent material through which the electromagnetic radiation is directed.

48. The device of claim 47, wherein the vapor-blocking layer is optically homogeneous with respect to electromagnetic radiation of the particular wavelength.

49. The device of claim 40, further comprising a means for introducing the selected fluid in vapor form at or near the fluid-transporting surface.

50. A method for controllably moving a droplet of a selected fluid across a surface of a solid substrate, comprising:
(a) depositing a droplet of a selected fluid on a solid substrate having a fluid-transporting surface and an opposing electromagnetic radiation-receiving surface, wherein the substrate is comprised of a material that is substantially transparent to electromagnetic radiation of a particular wavelength, and the droplet is placed on a first site of the fluid-transporting surface; and
(b) directing electromagnetic radiation having a particular wavelength toward the radiation-receiving surface and through the substrate to the fluid-transporting surface in a manner effective to optically move the droplet to a second site on the fluid-transporting surface.

51. The method of claim 50, wherein the fluid-transporting surface is coated at least in part with a lubricating layer and the droplet is placed on the lubricating layer.

52. The method of claim 51, wherein the lubricating layer is comprised of a fluid composition that is nonreactive and immiscible with the selected fluid.

53. The method of claim 52, wherein the fluid composition is hydrophobic.

54. The method of claim 50, wherein the droplet is free from vesicles, microspheres, or liposomes.

55. The method of claim 50, wherein the droplet is comprised of a vesicle, microsphere, or liposome.

56. The method of claim 50, wherein the droplet contains a plurality of solid particles.

57. The method of claim 56, wherein at least some or all of the solid particles are located on a surface of the droplet.

58. The method of claim 56, wherein at least some or all of the solid particles are located within the droplet.

59. The method of claim 50, wherein a contact angle of at least about 130° is formed between the droplet and the fluid-transporting surface.

60. The method of claim 59, wherein the contact angle is at least about 150°.

61. The method of claim 60, wherein the contact angle is at least about 170°.

62. The method of claim 50, wherein the droplet is optically moved away from the fluid-transporting surface during step (b).

63. The method of claim 50, further comprising, after (a), splitting the droplet into two droplets.

64. The method of claim 50, wherein the droplet has a volume of no greater than about 10 nanoliters.

65. The method of claim 64, wherein the droplet has a volume of no greater than about 100 picoliters.

66. The method of claim 65, wherein the droplet has a volume of no greater than about 1 picoliter.

67. The method of claim 50, further comprising reducing evaporative loss from the droplet while the droplet is on the fluid-transporting surface.

68. The method of claim 67, wherein evaporative loss is reduced by placing a vapor-blocking layer that is substantially impermeable to the selected fluid in vapor form over the droplet and the fluid-transporting surface so as to suppress release of the selected fluid in vapor form from the droplet.

69. The method of claim 68, wherein the vapor-blocking layer is comprised of a fluid composition that is immiscible and nonreactive with the selected fluid.

70. The method of claim 68, wherein the vapor-blocking layer is comprised of a solid material.

71. The method of claim 68, wherein evaporative loss is reduced by introducing the selected fluid in vapor form at or near the fluid-transporting surface.

72. The method of claim 50, wherein different contact angles are formed between the droplet and the fluid-transporting surface at the first and second sites.

73. The method of claim 50, wherein the same contact angle is formed between the droplet and the fluid-transporting surface at the first and second sites.

74. The method of claim 50, wherein the droplet is merged with additional fluid at the second site.

75. The method of claim 50, wherein the droplet contains a moiety that selectively binds to the fluid-transporting surface while the droplet is moved from the first to the second site.

76. The method of claim 50, wherein the directed radiation exhibits a Gaussian intensity profile.

77. The method of claim 50, wherein the directed radiation exhibits a non-Gaussian intensity profile.

78. The method of claim 50, wherein the directed radiation exhibits a rotationally symmetric intensity profile.

79. The method of claim 50, wherein the directed radiation exhibits a laterally symmetric intensity profile.

80. The method of claim 50, wherein the droplet is comprised of an aqueous liquid.

81. The method of claim 50, wherein the droplet contains a biomolecule.

82. The method of claim 50, wherein the biomolecule is peptidic or nucleotidic.

83. A method for controllably moving a droplet of a selected fluid across a surface of a solid substrate, comprising:

(a) depositing the droplet of a selected fluid on a first site of a fluid-transporting surface of a solid substrate;

(b) placing an optically homogeneous cover plate comprised of a material that is substantially transparent to electromagnetic radiation of a particular wavelength over the fluid-transporting surface, wherein the cover plate has an electromagnetic radiation-receiving surface and an opposing surface that is positioned in facing relationship to the fluid-transporting surface; and (c) directing electromagnetic radiation having a particular wavelength toward the radiation-receiving surface and through the cover plate to the fluid-transporting surface in a manner effective to optically move the droplet to a second site on the fluid-transporting surface.

84. A method for controllably moving a droplet of a selected fluid across a surface of a solid substrate, comprising:

(a) depositing the droplet of a selected fluid on a first site of a fluid-transporting surface of a solid substrate;

(b) directing electromagnetic radiation having a particular wavelength to the fluid-transporting surface in a manner effective to optically move the droplet to a second site on the fluid-transporting surface; and (c) reducing evaporative loss from the droplet while the droplet is on the fluid-transporting surface.

85. A method for controllably moving a fluid droplet across an interior surface of an enclosure, wherein the enclosure is formed at least in part by an optically homogeneous solid wall comprised of a material that is substantially transparent to electromagnetic radiation of a particular wavelength, comprising:

(a) depositing a droplet of a selected fluid on the interior surface of the enclosure at a first site; and (b) directing electromagnetic radiation of the particular wavelength through the solid wall in a manner effective to optically move the droplet across the interior surface to the second site.

86. The method of claim 85, wherein the enclosure is a tube.

* * * * *